United States Patent
Onuma et al.

(10) Patent No.: US 10,545,117 B2
(45) Date of Patent: Jan. 28, 2020

(54) SAMPLE ANALYSIS METHOD AND SOLUTION THEREFOR

(71) Applicant: ARKRAY, Inc., Kyoto-shi, Kyoto (JP)

(72) Inventors: Naotsugu Onuma, Kyoto (JP); Takanari Shigemitsu, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 411 days.

(21) Appl. No.: 14/991,149

(22) Filed: Jan. 8, 2016

(65) Prior Publication Data

US 2016/0209359 A1    Jul. 21, 2016

(30) Foreign Application Priority Data

Jan. 15, 2015 (JP) ................... 2015-006167
Dec. 22, 2015 (JP) ................... 2015-250367

(51) Int. Cl.
*G01N 27/447* (2006.01)
*G01N 33/72* (2006.01)

(52) U.S. Cl.
CPC . *G01N 27/44747* (2013.01); *G01N 27/44791* (2013.01); *G01N 33/721* (2013.01)

(58) Field of Classification Search
CPC .............. G01N 27/447; G01N 27/26; G01N 27/44769; G01N 27/44791; G01N 30/86–8696; B01L 2400/0415; B01L 2400/0421; B81B 1/00–008

See application file for complete search history.

(56) References Cited

U.S. PATENT DOCUMENTS

| | | | |
|---|---|---|---|
| 5,611,903 A | 3/1997 | Janssens et al. | |
| 2002/0125135 A1* | 9/2002 | Derand | B01L 3/502707 204/454 |
| 2004/0256232 A1* | 12/2004 | Jiang | B01J 20/28014 204/451 |
| 2006/0102478 A1* | 5/2006 | Robert | C07K 14/805 204/451 |
| 2010/0155242 A1 | 6/2010 | Nakayama et al. | |
| 2010/0175996 A1* | 7/2010 | Tanaka | G01N 27/447 204/451 |
| 2010/0282607 A1* | 11/2010 | Oishi | G01N 27/44747 204/450 |

(Continued)

FOREIGN PATENT DOCUMENTS

| | | |
|---|---|---|
| JP | 2006-145537 A | 6/2006 |
| JP | 2009-109230 A | 5/2009 |

(Continued)

OTHER PUBLICATIONS

Xuezhen Kang et al., "Chromatofocusing Using Micropellicular Column Packings with Computer-Aided Design of the Elution Buffer Composition", Analytical Chemistry, 2002, 74, 1038-1045.

(Continued)

*Primary Examiner* — Gurpreet Kaur
(74) *Attorney, Agent, or Firm* — Morgan, Lewis & Bockius LLP (57) ABSTRACT

A sample analysis method capable of improving separation accuracy of at least one of hemoglobin A2 and hemoglobin S and downsizing an analysis device is provided. The method includes separating hemoglobin in a sample in an alkaline solution containing a cationic polymer by capillary electrophoresis.

15 Claims, 5 Drawing Sheets

(56) References Cited

U.S. PATENT DOCUMENTS

2011/0000788 A1    1/2011  Deschamps et al.

FOREIGN PATENT DOCUMENTS

JP    2012-531609 A    12/2012
JP    2014-095638 A    5/2014

OTHER PUBLICATIONS

Cotton Frederic et al: "Evaluation of a capillary electrophoresis method for routine determination of hemoglobins A2 and F", Clinical Chemistry, American Association for Clinical Chemistry, Washington, DC, vol. 45, No. 2, Feb. 1, 1999, pp. 237-243.
Cotton F et al: "Electrophorese capillaire et hemoglobinopathies", Immuno Analyse Et Biologie Specialise, Ed. Scientifiques Elsevier, Paris, FR, vol. 21, No. 1, Feb. 1, 2006, pp. 45-50.

* cited by examiner

SAMPLE ANALYSIS METHOD AND SOLUTION THEREFOR

BACKGROUND OF THE INVENTION

1. Field of the Invention

The present disclosure relates to a method for analyzing a sample, a capillary electrophoresis solution, and a sample analysis kit.

2. Description of Related Art

Hemoglobin (Hb) is analyzed daily in the field of clinical laboratory testing. The type of hemoglobin to be analyzed differs depending on the purpose of the testing. HbA1c is well known as hemoglobin to be analyzed for the diagnosis and understanding of medical conditions associated with diabetes. Variant hemoglobins, which are typified by HbS (sickle-cell hemoglobin), HbC, HbD, and HbE, are used as the hemoglobins to be analyzed for the diagnosis of hemoglobinopathy. HbA2 and HbF (fetal hemoglobin) are widely used as the hemoglobins to be analyzed for the diagnosis of β thalassemia.

Such hemoglobin analyses are conducted by high-performance liquid chromatography (HPLC) including ion exchange chromatography, or capillary electrophoresis (CE) (for example, JP 2014-95638 A, JP 2006-145537 A, JP 2012-531609 A, JP 2009-109230 A, and Xuezhen Kang et al. (Analytical Chemistry, 2002, 74, 1038-1045)).

JP 2014-95638 A describes a hemoglobin analysis by cation exchange chromatography. Xuezhen Kang et al. describes a hemoglobin analysis by anion exchange chromatography. Such HPLC, however, requires a large and costly special device, making it difficult to downsize the device and achieve a cost reduction.

JP 2006-145537 A describes a hemoglobin analysis by free solution capillary electrophoresis (capillary zone electrophoresis: CZE) at an alkaline pH. JP 2012-531609 A describes a hemoglobin analysis by capillary electrophoresis at an alkaline pH and in the presence of a boronate compound. JP 2009-109230 A describes a hemoglobin analysis by cation exchange electrokinetic chromatography using a solution containing an anionic polymer as the pseudostationary phase.

SUMMARY OF THE INVENTION

The methods of JP 2014-95638 A and Xuezhen Kang et al. are both HPLC and thus require a large and costly special device, making it difficult to downsize the device and achieve a cost reduction.

The methods of JP 2006-145537 A and JP 2012-531609 A take a long time to complete analysis (e.g., eight minutes or more) and need a long capillary length (e.g., 20 cm or more), making it difficult to downsize the device.

β thalassemia patients often simultaneously suffer from hemoglobinopathy associated with HbS, and hence separation of HbS and HbA2 is required. Using the method of JP 2009-109230 A, however, it is difficult to separate HbA2 and the relatively major variant hemoglobin, HbS.

In one aspect, the present disclosure provides a method for analyzing a sample, a capillary electrophoresis solution and a sample analysis kit that are capable of improving the separation accuracy of at least one of HbS and HbA2, shortening the analysis time and downsizing the device.

In one aspect, the present disclosure relates to a method for analyzing a sample, including separating hemoglobin in the sample by capillary electrophoresis. The separation of hemoglobin is conducted in an alkaline solution containing a cationic polymer.

In one aspect, the present disclosure relates to a method for analyzing a sample, including: introducing the sample into a capillary channel filled with a running buffer; and applying a voltage to the whole or a part of the capillary channel for capillary electrophoresis so as to separate hemoglobin in the sample. The running buffer is an alkaline solution containing a cationic polymer.

In one aspect, the present disclosure relates to a capillary electrophoresis solution for hemoglobin separation analysis that is alkaline and contains a cationic polymer and water.

In one aspect, the present disclosure relates to a sample analysis kit, including: a container containing the capillary electrophoresis solution of the present disclosure; and an electrophoresis chip having a sample reservoir, a running buffer reservoir, and a capillary channel connecting the sample reservoir and the running buffer reservoir.

The present disclosure can provide a method for analyzing a sample capable of downsizing a device and improving the separation accuracy of at least one of HbS and HbA2, a capillary electrophoresis solution, and a sample analysis kit.

DETAILED DESCRIPTION OF THE INVENTION

In one aspect, the present disclosure is based on the finding that the respective fractions of hemoglobin (at least one of HbS and HbA2) in a sample can be separated with high accuracy in a short time by conducting capillary electrophoresis in an alkaline solution containing a cationic polymer.

Although it is uncertain why separation of hemoglobin by capillary electrophoresis in an alkaline solution containing a cationic polymer allows highly accurate separation of at least one of HbS and HbA2 in the sample in a short time, the mechanism can be considered as follows. The isoelectric point of hemoglobin is near neutral, and hence hemoglobin is negatively charged in an alkaline solution. The negatively charged hemoglobin moves to the positive electrode side when the negative electrode is brought into contact with the sample introduction side and a voltage is applied thereto. Meanwhile, the cationic polymer moves from the positive electrode side to the negative electrode side. The negatively charged hemoglobin interacts with the positively charged cationic polymer during electrophoresis. The respective fractions of hemoglobin have different degrees of negative charge in the alkaline solution. Such a difference in negative charge causes interaction differences between the respective fractions of hemoglobin and the cationic polymer, which consequently makes a difference in the electrophoresis speed between HbA2 and HbS. Thus, the separation accuracy of at least one of HbA2 and HbS is improved. The present disclosure, however, is not limited to these mechanisms.

[Cationic Polymer]

The "cationic polymer" in the present disclosure refers to a polymer having a cationic group or having a group that can be ionized into a cationic group. In one or more embodiments, the cationic polymer may be a homopolymer of a monomer having a cationic group, or a copolymer or a condensation polymer of a monomer having a cationic group and another monomer. In one or more embodiments, the cationic group may be, e.g., a group containing nitrogen. In one or more embodiments, examples of the cationic group include polymers having a cationic group, such as primary, secondary and tertiary amino groups, an imino group, and a quaternary ammonium salt group. Polymers having any of primary, secondary and tertiary amino groups are preferred, and polymers having a primary amino group are more preferred from the viewpoint of improving the accuracy of analysis. In one or more embodiments, the cationic polymer is preferably water soluble. In one or more embodiments, the cationic polymer is preferably a straight-chain polymer from the viewpoint of improving the accuracy of analysis. The cationic polymer may be used alone or in a combination of two or more kinds.

In one or more embodiments, examples of the cationic polymer having any of primary, secondary and tertiary amino groups, or having a group that can be ionized into any of primary, secondary and tertiary amino groups include polyallylamine, polyvinylamine, polylysine, polyarginine, polyhistidine, polyornithine, polydiallylamine, and polymethyldiallylamine.

In one or more embodiments, an example of the cationic polymer having an imino group, or having a group that can be ionized into an imino group is polyethyleneimine.

In one or more embodiments, examples of the cationic polymer having a quaternary ammonium salt group, or having a group that can be ionized into a quaternary ammonium salt group include polyquaternium, and a dimethylamine-epichlorohydrin copolymer. In the present disclosure, "polyquaternium" refers to a cationic polymer including a constituent unit derived from a monomer having a quaternary ammonium group. The definition of "polyquaternium" can be confirmed in the INCI (International Nomenclature for Cosmetic Ingredients) directory. In one or more embodiments, examples of the polyquaternium include: polydiallyldimethylammonium salts such as polyquaternium-6 (poly (diallyldimethylammonium chloride), polyquaternium-7 (copolymer of acrylamide and diallyldimethylammonium chloride), polyquaternium-4 (diallyldimethylammonium chloride-hydroxyethyl cellulose copolymer), and polyquaternium-22 (copolymer of acrylic acid and diallyldimethylammonium chloride); and polyquaternium-2 (poly[bis (2-chloroethyl)ether-alt-1,3-bis[3-(dimethylamino)propyl] urea]). In one or more embodiments, the dimethylamine-epichlorohydrin copolymer may include a constituent unit other than dimethylamine-epichlorohydrin, and for example it may include ethylene diamine and the like.

Further, in one or more embodiments, the cationic polymer may be a cationic polymer of an onium salt, such as a phosphonium salt, an oxonium salt, a sulfonium salt, a fluoronium salt, and a chloronium salt.

In one or more embodiments, an example of the cationic polymer having a hydrazide group, or having a group that can be ionized into a hydrazide group is aminopolyacrylamide.

The cationic polymer is preferably polyethyleneimine, polyallylamine, polylysine, and a combination thereof, and more preferably polyallylamine from the viewpoint of improving the accuracy of analysis and shortening a measurement time.

In one or more embodiments, the weight-average molecular weight of the cationic polymer is 1000 or more, 5000 or more, or 10000 or more from the viewpoint of improving the accuracy of analysis, and 500000 or less, or 300000 or less from the viewpoint of preventing an increase in solution viscosity.

[Alkaline Solution Containing Cationic Polymer]

The "alkaline solution containing a cationic polymer" in the present disclosure refers to an alkaline solution in which a cationic polymer is dispersed or dissolved in a medium. In one or more embodiments, the medium may be, e.g., water. In one or more embodiments, examples of the water include distilled water, ion-exchanged water, pure water, and ultra-pure water. In one or more embodiments, the alkaline solution containing a cationic polymer is an alkaline aqueous solution containing a cationic polymer and water.

In one or more embodiments, the pH of the alkaline solution is preferably higher than the isoelectric point of hemoglobin, and more preferably higher than the isoelectric point of at least one of HbS and HbA2. The isoelectric point of HbS is 7.2 to 7.3, and the isoelectric point of HbA2 is 7.4 to 7.5. Hence, in one or more embodiments, the pH of the alkaline solution is 7.5 or higher, and preferably 8.5 or higher, or 9.5 or higher from the viewpoint of improving the accuracy of analysis and shortening the measurement time. It is preferably 12.0 or lower, or 11.0 or lower from the viewpoint of preventing denaturation of hemoglobin. The above pH is the pH of the alkaline solution at 25° C. that is measured after 30-minute immersion of electrodes of a pH meter.

In one or more embodiments, the content of the cationic polymer in the alkaline solution is 0.01% (W/V) or more, 0.05% (W/V) or more, or 0.1% (W/V) or more from the viewpoint of improving the accuracy of analysis, and 10.0% (W/V) or less, 8.0% (W/V) or less, or 5.0% (W/V) or less from the viewpoint of preventing an increase in solution viscosity.

[Sample]

In one or more non-limiting embodiments, the "sample" of the present disclosure may be, e.g., a sample prepared from a sample material, or the sample material itself. In one or more non-limiting embodiments, the sample material may be, e.g., a sample containing hemoglobin, or a biological sample. In one or more non-limiting embodiments, the biological sample may be, e.g., blood, or a blood-derived material containing erythrocyte components. The blood may be, e.g., blood sampled from a living body, and examples of the same include, in one or more non-limiting embodiments, blood of an animal, blood of a mammal, and blood of a human. The blood-derived material containing erythrocyte components may be, e.g., a material that is separated or prepared from blood and contains erythrocyte components, and examples of the same include, in one or more non-limiting embodiments, a fraction of blood cells obtained by removing plasma, a concentrate of blood cells, freeze-dried blood or blood cells, a hemolyzed sample obtained by hemolyzing whole blood, centrifuged blood, blood obtained through spontaneous sedimentation, and washed blood cells.

[Sample Analysis Method]

In one aspect, the present disclosure relates to a method for analyzing a sample (hereinafter, also referred to as the "sample analysis method"). In one aspect, the sample analysis method of the present disclosure includes separating, in an alkaline solution containing a cationic polymer, hemoglobin in a sample by capillary electrophoresis. Further, in one aspect, the sample analysis method of the present disclosure includes introducing a sample into a capillary channel filled with a running buffer; and applying a voltage to the whole or a part of the capillary channel for capillary electrophoresis so as to separate hemoglobin in the sample. The running buffer is an alkaline solution containing a cationic polymer.

In one or more embodiments, the present disclosure can improve the separation accuracy of at least one of HbS and HbA2. In one or more not particularly limiting embodiments, the present disclosure can separate at least one of HbS and HbA2 in a short time in a small device, and preferably provide effects of improving the separation accuracy and the separation speed of HbS and HbA2.

In one or more embodiments, the separation of hemoglobin includes separating at least one of HbS and HbA2, and preferably includes separating HbS and HbA2. Further, in one or more embodiments, the separation of hemoglobin includes separating at least one of HbS and HbA2, and at least one of HbF, HbC, HbD, and HbE.

In one or more embodiments, the sample analysis method of the present disclosure includes separating hemoglobin using a running buffer that is an alkaline solution containing a cationic polymer.

In one or more embodiments, hemoglobin is separated using a capillary channel. In one or more embodiments, the capillary channel is a tube having an inner diameter of 100 μm or less. The tube may have any cross-sectional shape such as a circle or a rectangle. In one or more embodiments, the length of the capillary channel is 10 mm or more, or 20 mm or more, and 150 mm or less, or 60 mm or less. In one or more embodiments, the inner diameter of the capillary channel is 10 μm or more, or 25 μm or more, and 100 μm or less, or 75 μm or less.

In one or more embodiments, the capillary channel is preferably coated with a cationic substance or an anionic substance. Such coating with a cationic substance can positively charge the inner wall of the capillary channel, thereby easily causing an electroosmotic flow that runs from the negative electrode side toward the positive electrode side of the capillary channel. When the capillary channel is coated with an anionic substance, the capillary channel is negatively charged. However, the cationic polymer contained in the alkaline solution is bonded to the negatively-charged capillary channel, and the inner wall of the capillary channel is positively charged, thereby easily causing an electroosmotic flow that runs from the negative electrode side toward the positive electrode side of the capillary channel in the same manner as described above. In one or more embodiments, the sample analysis method of the present disclosure includes causing a liquid flow from the negative electrode side toward the positive electrode side of the capillary channel. In one or more embodiments, the liquid flow is preferably an electroosmotic flow.

In one or more embodiments, the cationic substance may be, e.g., the above cationic polymer, or a silane coupler having a cationic functional group. A polymer having a quaternary ammonium salt group is preferred from the viewpoint of improving the accuracy of analysis.

In one or more embodiments, the anionic substance may be, e.g., polysaccharides having an anionic group, or a silane coupler having an anionic functional group. In one or more embodiments, examples of the polysaccharides having an anionic group include sulfated polysaccharides, carboxylated polysaccharides, sulfonated polysaccharides, and phosphorylated polysaccharides. In one or more non-limiting embodiments, examples of the sulfated polysaccharides include chondroitin sulfate, heparin, heparan, fucoidan, and salts thereof. Examples of the carboxylated polysaccharides include alginic acid, hyaluronic acid, and salts thereof. When the polysaccharide having an anionic group is a salt, examples of the counter ion include ions of an alkali metal, an alkaline earth metal, an amine compound, and an organic base. In one or more embodiments, examples of the salts of carboxylated polysaccharides include sodium salt, potassium salt, lithium salt, calcium salt, ammonium salt, tris salt, arginine salt, lysine salt, histidine salt, trishydroxymethyl aminomethane salt, dimethylaminoethanol salt, triethanolamine salt, diethanolamine salt, and creatinine salt. In one or more non-limiting embodiments, examples of the carboxylated polysaccharides include alginic acid, and salts thereof (e.g., sodium alginate).

In one or more embodiments, the sample analysis method of the present disclosure is preferably conducted using a capillary electrophoresis chip having a microchipped capillary channel. In one or more embodiments, the electrophoresis chip has a length of 10 to 200 mm, a width of 1 to 60 mm, and a thickness of 0.3 to 5 mm, or a length of 30 to 70 mm, a width of 1 to 60 mm, and a thickness of 0.3 to 5 mm. A non-limiting embodiment of the capillary electrophoresis chip will be described later.

In one or more embodiments, the sample analysis method of the present disclosure includes applying a voltage to the whole or a part of the capillary channel for capillary electrophoresis. In one or more embodiments, the sample analysis method of the present disclosure includes bringing a negative electrode into contact with the sample introduction side and applying a voltage thereto, and preferably includes bringing a negative electrode and a positive electrode into contact with the sample introduction side and the running buffer supply side, respectively, and applying a voltage thereto.

In one or more embodiments, the sample is preferably prepared using an alkaline solution containing a cationic polymer from the viewpoint of improving the separation accuracy. In one or more embodiments, the sample analysis method of the present disclosure includes diluting the sample material using an alkaline solution containing a cationic polymer so as to prepare the sample. In one or more embodiments, the dilution rate is 1.2 to 100 times, 2 to 60 times, or 3 to 50 times. When the sample material contains an ion component in such a concentration that the ion component may affect the separation capability, in one or more embodiments, the dilution rate is 2 to 1000 times, 5 to 300 times, or 10 to 200 times. In one or more embodiments, the composition of the alkaline solution containing a cationic polymer used for preparation of the sample may be the same or different from that of the liquid (running buffer) to be filled in the capillary channel.

In one or more embodiments, the alkaline solution may include at least a non-detergent amphoteric ionic substance, or a pH buffer substance, or a preserving agent for preventing development of microorganisms, etc. In one or more embodiments, examples of the preserving agent include sodium azide, ethylparaben, and proclin.

In one or more embodiments, the non-detergent amphoteric ionic substance is preferably a substance not having a pH buffer action, and more preferably a substance not exhibiting or practically not exhibiting a pH buffer action at the pH of the electrophoresis condition, from the viewpoint of improving the accuracy of analysis. In one or more embodiments, the non-detergent amphoteric ionic substance is preferably a non-detergent betaine, more preferably a non-detergent sulfobetaine or a non-detergent carboxy betaine, further preferably a non-detergent substance having a quaternary ammonium cation and a sulfo group ($-SO_3-$) or a carboxyl group ($-COO-$) at sites not adjacent to each other in the same molecule, and further more preferably a non-detergent sulfobetaine (NDSB), from the viewpoint of improving the accuracy of analysis. In one or more non-limiting embodiments, examples of the NDSB include NDSB-201 (3-(1-Pyridinio)-1-propanesulfonate, $C_8H_{11}NO_3S$), NDSB-211 (Dimethyl(2-hydroxyethy)ammonium propane sulfonate, $C_7H_{17}NO_4S$), NDSB-221 (3-(1-methylpiperidin-1-ium-1-yl)propane-1-sulfonate, $C_9H_{19}NO_3S$), NDSB-195 (Dimethylethylammonium propane sulfonate, $C_7H_{17}NO_3S$), and NDSB-256 (Dimethylbenzylammonium propane sulfonate, $C_{12}H_{19}NO_3S$).

In one or more non-limiting embodiments, the pH buffer substance may be any substance that has a pH buffer action at the pH of the electrophoresis condition. In one or more non-limiting embodiments, examples of the pH buffer substance include BES (N,N-Bis(2-hydroxyethyl)-2-aminoethanesulfonic acid), MOPS (3-Morpholinopropanesulfonic acid), TES (N-Tris(hydroxymethyl)methyl-2-aminoethanesulfonic acid), HEPES (2-[4-(2-Hydroxyethyl)-1-piperazinyl]ethanesulfonic acid), TRICINE (N-[Tris(hydroxymethyl)methyl]glycine), PIPES (Piperazine-1,4-bis(2-ethanesulfonic acid)), POPSO (Piperazine-1,4-bis(2-hydroxy-3-propanesulfonic acid), dihydrate), carbonic acid, phosphoric acid, boric acid, glycine, alanine, leucine, arginine, lysine, histidine, taurine, aspartic acid, asparagine, hydroxyproline, proline, threonine, serine, glutamic acid, glutamine, valine, cysteine, methionine, isoleucine, leucine, tyrosine, phenylalanine, ornithine, tryptophan, trishydroxymethylaminomethane, dimethylaminoethanol, triethanolamine, diethanolamine, monoethanolamine, N-methylamino ethanol, creatinine, imidazole, barbital, ammonia, ethylamine, diethylamine, and triethylamine. In one or more non-limiting embodiments, examples of the other pH buffer substances include diamine compounds such as 1,4-diaminobutane.

In one or more embodiments, the sample analysis method of the present disclosure includes detecting fractions of hemoglobin separated by capillary electrophoresis. In one or more embodiments, the detection can be conducted by detecting fractions of hemoglobin separated by capillary electrophoresis using an optical process. The detection using an optical process may be, e.g., a measurement of absorbance. In one or more embodiments, the wavelength of the absorbance may be, e.g., 415 nm.

In one or more embodiments, the sample analysis method of the present disclosure may further include analyzing an electropherogram obtained by an optical process. When separating (conducting capillary electrophoresis) sample components while sampling continuously, it is difficult to individually identify each hemoglobin in the sample based on the obtained electropherogram. However, by an analysis operation of the electropherogram, each hemoglobin in the sample can be separated and analyzed individually. This analysis operation of the electropherogram may include: conducting an operation on the electropherogram to obtain electropherograms that are separated based on the mobility (separation time); and determining the proportion of components of the hemoglobin in the sample on the basis of the height and/or area of each peak of the obtained electropherogram. Examples of the operation include differential operation and difference operation.

In one aspect, the present disclosure relates to a method for measuring hemoglobin in a sample, including measuring hemoglobin in the sample using the sample analysis method of the present disclosure. The sample is as described above. In one or more non-limiting embodiments, the measurement method of the present disclosure includes measuring at least one of HbS and HbA2, the HbS serving as an indicator of hemoglobinopathy and HbA2 serving as an indicator of β thalassemia. Therefore, in another aspect, the present disclosure relates to a method for measuring hemoglobin, including measuring at least one of HbS and HbA2 using the sample analysis method of the present disclosure. Preferably, the measurement method of the present disclosure is a method including separating and measuring HbS and HbA2 using the sample analysis method of the present disclosure, from the viewpoint of simultaneously diagnosing β thalassemia and hemoglobinopathy.

[Capillary Electrophoresis Solution]

In one aspect, the present disclosure relates to a capillary electrophoresis solution that is alkaline and contains a cationic polymer and water. In the present disclosure, in one or more embodiments, the term "capillary electrophoresis solution" refers to a solution filling a capillary channel in capillary electrophoresis. In one or more embodiments, the capillary electrophoresis solution of the present disclosure may be used as a solution for preparing the sample. In one or more embodiments, the capillary electrophoresis solution of the present disclosure can be used for the sample analysis method of the present disclosure, contributing to the improvement of the accuracy of analysis of the sample, and preferably contributing to the improvement of the accuracy of analysis and the shortening of the measurement time.

The capillary electrophoresis solution of the present disclosure may be the above alkaline solution containing a cationic polymer.

[Sample Analysis Kit]

In one aspect, the present disclosure relates to a sample analysis kit, including: a container containing the capillary electrophoresis solution of the present disclosure; and a capillary electrophoresis chip. In the sample analysis kit of the present disclosure, the capillary electrophoresis chip has a sample reservoir, a running buffer reservoir, and a capillary channel connecting the sample reservoir and the running buffer reservoir. In one or more embodiments, the sample analysis kit of the present disclosure can be used for the sample analysis method of the present disclosure, contributing to the improvement of the accuracy of analysis of the sample, and preferably contributing to the improvement of the accuracy of analysis and the shortening of the measurement time. The explanations and embodiments of the capillary electrophoresis solution, the capillary channel, and the capillary electrophoresis chip are as described above.

[Sample Analysis System]

In one aspect, the present disclosure relates to a sample analysis system using a capillary electrophoresis chip, including: a holding portion that holds a container containing the capillary electrophoresis solution of the present disclosure and a capillary electrophoresis chip; a power supply portion that applies a voltage to the capillary electrophoresis chip; and a control portion that controls switching of the polarity of a voltage applied to the capillary electrophoresis chip.

Hereinafter, a non-limiting embodiment of the sample analysis method of the present disclosure will be described.

Embodiment 1

Figure 1:
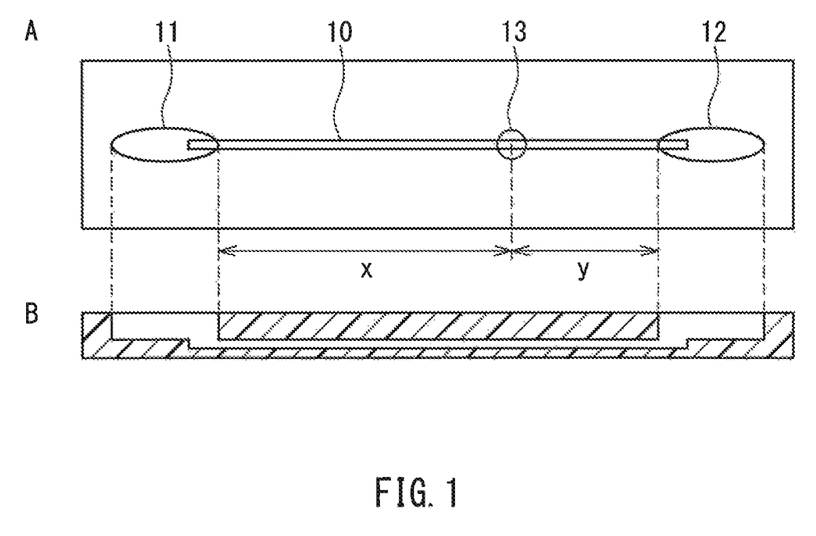
FIG. 1 is an embodiment of a capillary electrophoresis chip, where section A is showing a top view of an embodiment of a capillary electrophoresis chip and section B is showing a cross-sectional view of the electrophoresis chip shown in section A.

The following exemplifies a case in which a capillary electrophoresis chip shown in FIGS. 1A and 1B is used and whole blood is used as a sample material.

FIG. 1 is a schematic diagram showing one or more non-limiting embodiments of the configuration of the capillary electrophoresis chip used in the sample analysis method of the present disclosure. Section A of FIG. 1 is a top view showing an embodiment of a capillary electrophoresis chip. Section B of FIG. 1 is a cross-sectional view of the electrophoresis chip shown in Section A of FIG. 1.

The capillary electrophoresis chip shown in FIG. 1 has a capillary channel 10, a sample reservoir 11, and a running buffer reservoir 12. The capillary channel 10 connects the sample reservoir 11 and the running buffer reservoir 12. A detecting portion 13 is formed in the capillary channel 10. The length and the inner diameter of the capillary channel 10 as well as the size of the capillary electrophoresis chip are as described above.

The capacity of each of the sample reservoir 11 and the running buffer reservoir 12 is determined appropriately in accordance with the inner diameter, the length, etc., of the capillary channel 10. In one or more embodiments, the each capacity is in the range from 1 to 1000 mm$^3$, and preferably from 5 to 100 mm$^3$. Each of the sample reservoir 11 and the running buffer reservoir 12 may be provided with an electrode for applying a voltage to both ends of the capillary channel 10.

The position for the measurement, i.e., the length required for separation (the distance from the sample reservoir 11 to the detecting portion 13, "x" in Section A of FIG. 1), can be determined suitably on the basis of the length of the capillary channel 10, etc. When the length of the capillary channel 10 (x+y in Section A of FIG. 1) is in the range from 10 to 150 mm, the distance (x) to the detecting portion 13 is in the range from 5 to 140 mm, 10 to 100 mm, or 15 to 50 mm.

The material of the capillary channel 10 may be, e.g., glass, fused silica, or plastic. Examples of the plastic include polymethyl methacrylate (PMMA), polycarbonate, polystyrene, polytetrafluoroethylene (PTFE), and polyetheretherketone (PEEK).

The capillary channel 10 may be a commercially available capillary. The capillary electrophoresis chip may be a commercially available chip for HbA1c.

The following describes an exemplary sample analysis method using the capillary electrophoresis chip shown in FIG. 1.

First, the running buffer reservoir 12 of the capillary electrophoresis chip is filled with the capillary electrophoresis solution of the present disclosure (the alkaline aqueous solution containing a cationic polymer) as a running buffer so that the capillary channel 10 is filled with the running buffer by capillary action.

Next, a sample is placed in the sample reservoir 11 of the capillary electrophoresis chip filled with the running buffer.

The sample to be placed in the sample reservoir 11 can be prepared by diluting whole blood as a sample material with the capillary electrophoresis solution of the present disclosure.

Then, a negative electrode and a positive electrode are brought into contact with the sample reservoir 11 and the running buffer reservoir 12, respectively, and a voltage is applied to both ends of the capillary channel 10, i.e., between the sample reservoir 11 and the running buffer reservoir 12. Thereby, the sample including hemoglobin is introduced from the sample reservoir 11 to the capillary channel 10, and hemoglobin is separated while the sample moves from the sample reservoir 11 toward the running buffer reservoir 12. In one or more non-limiting embodiments, the voltage to be applied to the both ends of the capillary channel 10 is in the range from 500 to 10000 V, or 500 to 5000 V.

Thereafter, a measurement is conducted at a detecting portion 13. For example, the measurement can be conducted by an optical process such as measurement of absorbance at a wavelength of 415 nm.

By the analysis as described above, it is possible to measure hemoglobin, and preferably it is possible to separate and measure HbS and/or HbA2. Furthermore, by the analysis operation of the obtained electropherogram, it is possible to measure, e.g., the rate (%) and the amount of each hemoglobin separated. Therefore, the sample analysis method of the present disclosure can be utilized for the prevention, diagnosis, treatment, etc., of hemoglobinopathy and β thalassemia.

The present disclosure can relate to one or more embodiments described below.

[1] A method for analyzing a sample, including separating hemoglobin in the sample by capillary electrophoresis,
wherein the separation of hemoglobin is conducted in an alkaline solution containing a cationic polymer.

[2] A method for analyzing a sample, including:
introducing a sample into a capillary channel filled with a running buffer; and
applying a voltage to a whole or a part of the capillary channel for capillary electrophoresis so as to separate hemoglobin in the sample,
wherein the running buffer is an alkaline solution containing a cationic polymer.

[3] The method for analyzing a sample according to [1] or [2], further including preparing the sample using an alkaline solution containing a cationic polymer.

[4] The method for analyzing a sample according to any one of [1] to [3], wherein the cationic polymer includes at least one selected from the group consisting of primary, secondary and tertiary amino groups, an imino group, a quaternary ammonium salt group, a hydrazide group, and a combination thereof.

[5] The method for analyzing a sample according to any one of [1] to [4], wherein a pH of the alkaline solution is in a range from 7.5 to 12.0.

[6] The method for analyzing a sample according to any one of [1] to [5], wherein the alkaline solution further includes one selected from the group consisting of a non-detergent amphoteric ionic substance, a pH buffer substance, and a combination thereof.

[7] The method for analyzing a sample according to any one of [2] to [6], wherein a cationic substance or an anionic substance is bound to the capillary channel.

[8] The method for analyzing a sample according to any one of [2] to [7], further including causing a liquid flow from a negative electrode side toward a positive electrode side in the capillary channel.

[9] The method for analyzing a sample according to any one of [2] to [8], further including bringing a negative electrode into contact with a sample introduction side and applying a voltage thereto.

[10] A capillary electrophoresis solution for hemoglobin separation analysis that is alkaline and contains a cationic polymer and water.

[11] The capillary electrophoresis solution according to [10], wherein the cationic polymer includes at least one selected from the group consisting of primary, secondary and tertiary amino groups, an imino group, a quaternary ammonium salt group, a hydrazide group, and a combination thereof.

[12] The capillary electrophoresis solution according to [10] or [11], further including one selected from the group consisting of a non-detergent amphoteric ionic substance, a pH buffer substance, and a combination thereof.

[13] A sample analysis kit, including:
a container containing the capillary electrophoresis solution according to any one of [10] to [12]; and
an electrophoresis chip having a sample reservoir, a running buffer reservoir, and a capillary channel connecting the sample reservoir and the running buffer reservoir.

Hereinafter, the present disclosure will be described further based on examples and comparative examples. However, the present disclosure is not limited to the following examples.

EXAMPLES

Example 1

<Preparation of Electrophoresis Solution>
An electrophoresis solution 1 was prepared by adding the following substances to pure water.
[Electrophoresis Solution 1]
1.0% (W/V) polyethyleneimine (manufactured by Wako Pure Chemical Industries, Ltd., weight-average molecular weight: 70000)
0.02% (W/V) sodium azide
500 mM NDSB-201 (non-detergent sulfobetain, 3-(1-pyridinio)-1-propanesulfonate)
3-hydroxypropanesulfonic acid (for pH adjustment) pH 9.0
<Hemoglobin Sample>
Two kinds of the following hemoglobin samples were prepared:
whole blood derived from β thalassemia patients not containing HbS; and
control specimen containing HbA, HbA2, HbS, and HbF (manufactured by Bio-Rad Laboratories, Inc.).
<Separation Device and Measurement Device>
A resin chip having the capillary channel 10 structured as shown in FIG. 1 was used as a separation device (channel: width 40 µm, height 40 µm, length 30 mm, separation length 20 mm). The capacity of each of the sample reservoir 11 and the running buffer reservoir 12 was 10 µL. The inner wall of the capillary channel was coated with polydiallyl dimethylammonium chloride.
An electrophoresis device manufactured by ARKRAY, Inc. was used as a measurement device.
<Capillary Electrophoresis>
The capillary electrophoresis was conducted by a continuous sample introducing method in the procedure described below.

1. 9 µL of the electrophoresis solution 1 was added to the running buffer reservoir 12 of the chip, so that the capillary channel 10 was filled with the electrophoresis solution 1.
2. 9 µL of the sample diluted 41 times with the electrophoresis solution 1 was added to the sample reservoir 11 of the chip.
3. A negative electrode and a positive electrode were brought into contact with the sample reservoir 11 and the running buffer reservoir 12, respectively, and a voltage of 1000 V was applied thereto so as to start electrophoresis.
4. Absorbance at 415 nm was measured at the detecting portion 13 so as to obtain an electropherogram. The electrophoresis was conducted for 60 seconds.

Figure 2A:
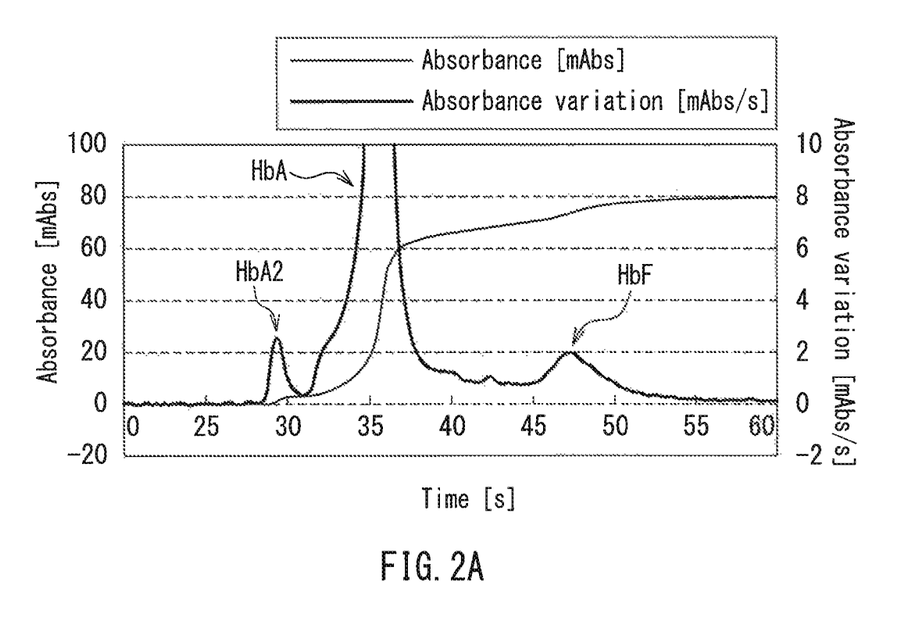
FIGS. 2A and 2B are exemplary electropherograms obtained by capillary electrophoresis in Example 1. The sample of FIG. 2A is whole blood derived from β thalassemia patients, and the sample of FIG. 2B is a control specimen.
Figure 2B:
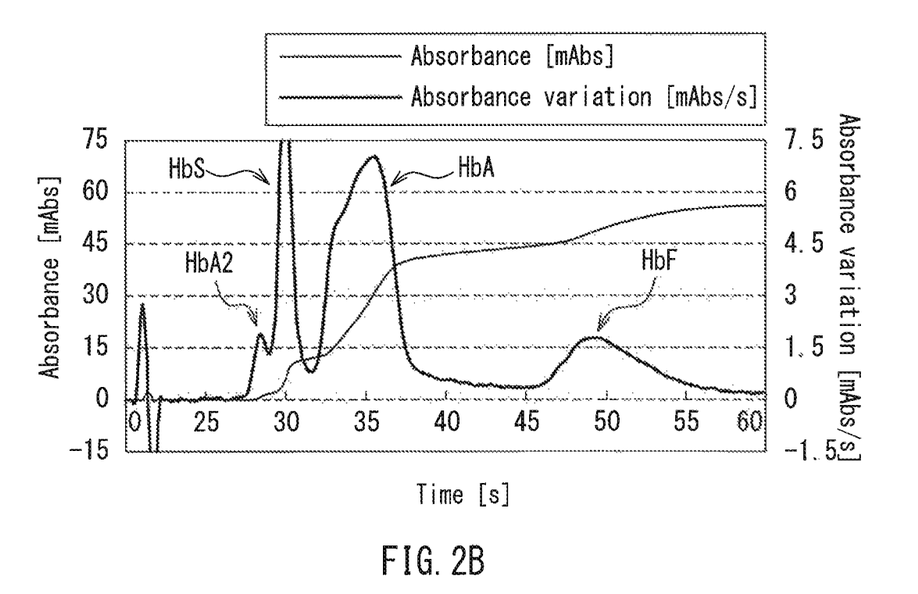

FIGS. 2A and 2B show the results. FIG. 2A is the result obtained using the whole blood derived from β thalassemia patients, and FIG. 2B is the result obtained using the control specimen.

As shown in FIGS. 2A and 2B, in both of the samples, the alkaline electrophoresis solution containing polyethyleneimine allowed separation of HbA2, HbS, HbA, and HbF within 60 seconds with an effective capillary length of 20 mm.

Example 2

The measurement was conducted in the same manner as in Example 1 except that an electrophoresis solution 2 below was added to the running buffer reservoir 12 instead of the electrophoresis solution 1, an electrophoresis solution 3 below was used to dilute the sample instead of the electrophoresis solution 1, and the measurement time was 75 seconds.
[Electrophoresis Solution 2]
1.0% (W/V) polyallylamine (manufactured by NITTOBO MEDICAL CO., LTD., weight-average molecular weight: 25000)
0.02% (W/V) sodium azide
500 mM NDSB-201
3-hydroxypropanesulfonic acid (for pH adjustment) pH 9.8
[Electrophoresis Solution 3]
1.0% (W/V) polyallylamine (manufactured by NITTOBO MEDICAL CO., LTD., weight-average molecular weight: 25000)
0.02% (W/V) sodium azide
3-hydroxypropanesulfonic acid (for pH adjustment) pH 9.8

Figure 3A:
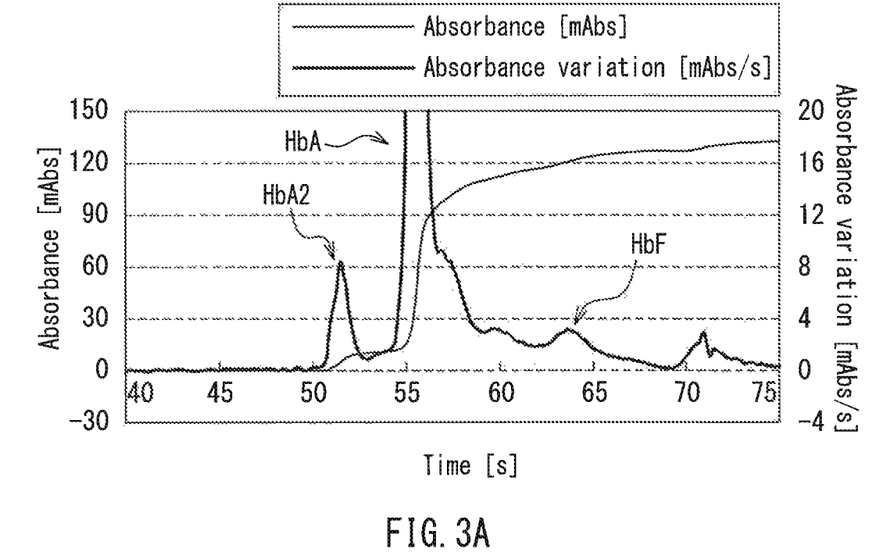
FIGS. 3A and 3B are exemplary electropherograms obtained by capillary electrophoresis in Example 2. The sample of FIG. 3A is whole blood derived from β thalassemia patients, and the sample of FIG. 3B is a control specimen.
Figure 3B:
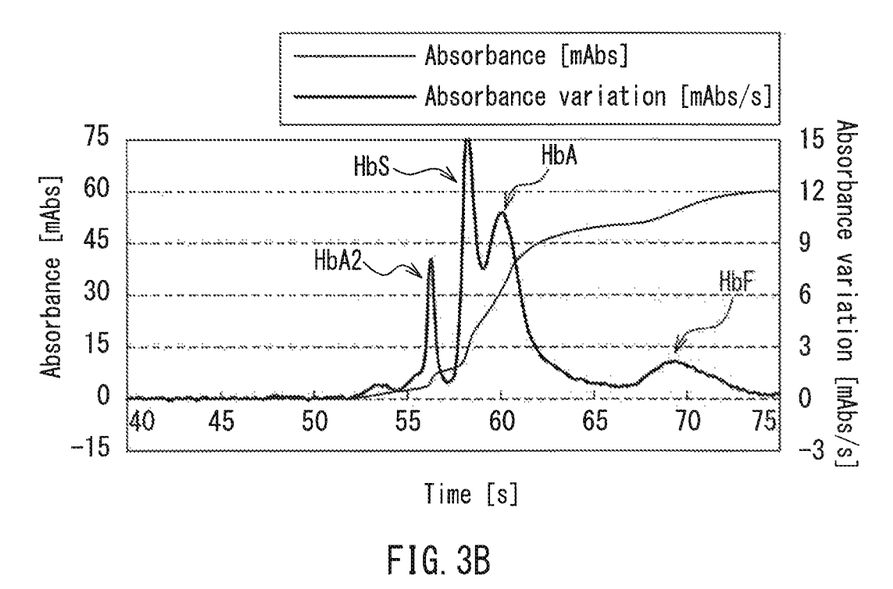

FIGS. 3A and 3B show the results. FIG. 3A is the result obtained using the whole blood derived from β thalassemia patients, and FIG. 3B is the result obtained using the control specimen.

As shown in FIGS. 3A and 3B, in both of the samples, the alkaline electrophoresis solution containing polyallylamine allowed separation of HbA2, HbS, HbA, and HbF within 75 seconds with an effective capillary length of 20 mm.

Example 3

The measurement was conducted in the same manner as in Example 1 except that an electrophoresis solution 4 below was used instead of the electrophoresis solution 1, the applied voltage was 1500 V, and the measurement time was 45 seconds. The control specimen of Example 1 was used as a hemoglobin sample.

[Electrophoresis Solution 4]
  100 mM arginine
  1.0% (W/V) polyL-lysine hydrochloride (manufactured by PEPTIDE INSTITUTE, INC., weight-average molecular weight: 8000 or more)
  0.02% (W/V) sodium azide
  3-hydroxypropanesulfonic acid (for pH adjustment) pH 9.8

Figure 4:
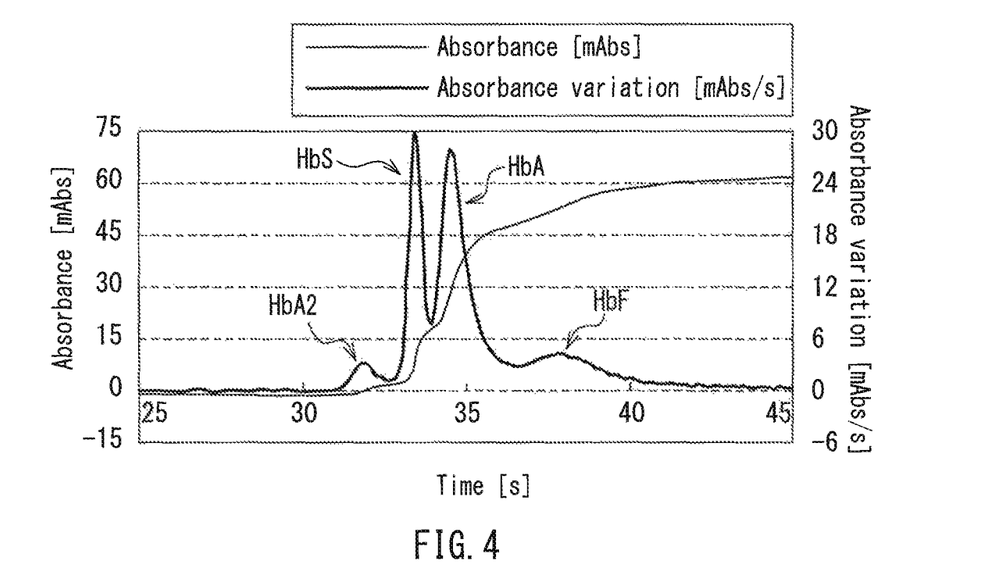
FIG. 4 is an exemplary electropherogram obtained by capillary electrophoresis in Example 3 (sample: control specimen).

FIG. 4 shows the results. As shown in FIG. 4, the alkaline electrophoresis solution containing polyL-lysine allowed separation of HbA2, HbS, HbA, and HbF within 45 seconds with an effective capillary length of 20 mm.

Example 4

The measurement was conducted in the same manner as in Example 3 except that an electrophoresis solution 5 below was used instead of the electrophoresis solution 4, and the measurement time was 80 seconds.

[Electrophoresis Solution 5]
  100 mM arginine
  0.25% (W/V) polyethyleneimine (manufactured by Wako Pure Chemical Industries, Ltd., weight-average molecular weight: 1800)
  0.75% (W/V) polyallylamine (manufactured by NITTOBO MEDICAL CO., LTD., weight-average molecular weight: 150000)
  3-hydroxypropanesulfonic acid (for pH adjustment) pH 9.8

Figure 5:
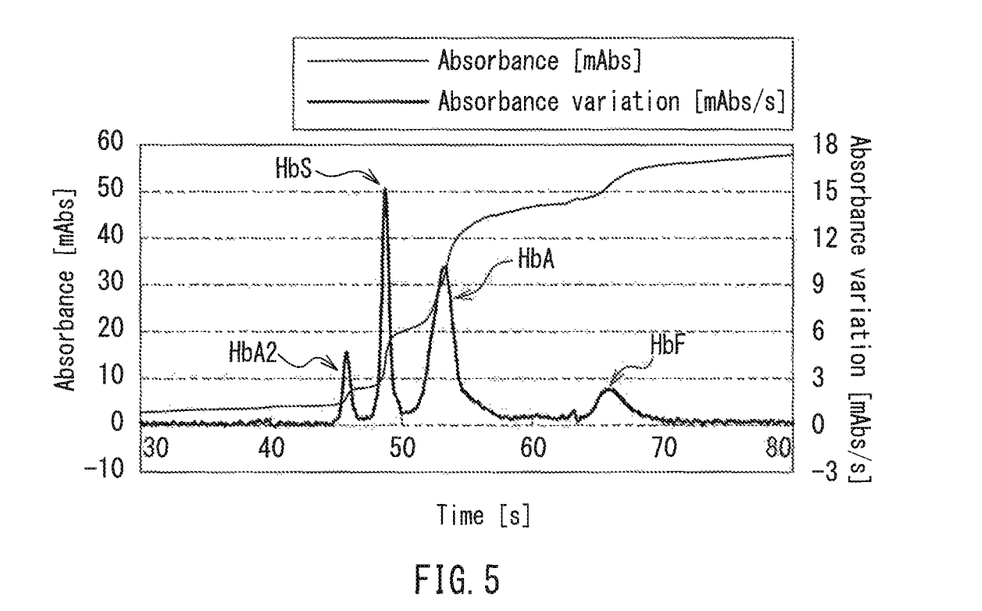
FIG. 5 is an exemplary electropherogram obtained by capillary electrophoresis in Example 4 (sample: control specimen).

FIG. 5 shows the results. As shown in FIG. 5, the alkaline electrophoresis solution containing polyethyleneimine and polyallylamine allowed separation of HbA2, HbS, HbA, and HbF within 70 seconds with an effective capillary length of 20 mm.

Comparative Example 1

The measurement was conducted in the same manner as in Example 1 except that an electrophoresis solution 6 below was used instead of the electrophoresis solution 1, the applied voltage was 1500 V, and the measurement time was 70 seconds. The control specimen of Example 1 was used as a hemoglobin sample.

[Electrophoresis Solution 6]
  20 mM MES
  1.0% (W/V) polyethyleneimine (manufactured by Wako Pure Chemical Industries, Ltd., weight-average molecular weight: 70000)
  0.02% (W/V) sodium azide
  3-hydroxypropanesulfonic acid (for pH adjustment) pH 6.0

Figure 6:
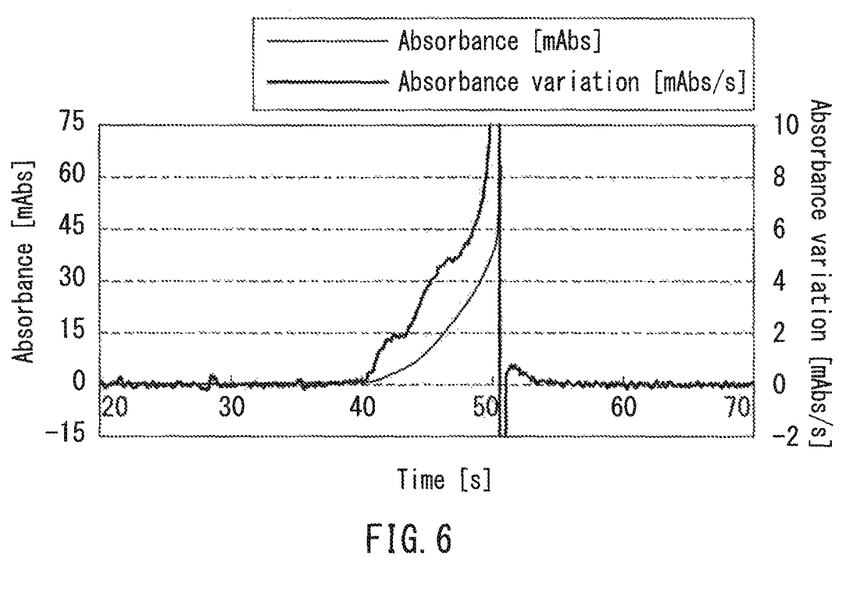
FIG. 6 is an exemplary electropherogram obtained by capillary electrophoresis in Comparative Example 1 (sample: control specimen).

FIG. 6 shows the results. As shown in FIG. 6, it was confirmed that none of HbA2, HbS, HbA, and HbF were separated by the electrophoresis solution (pH 6.0) that contained polyethyleneimine as a cationic polymer but was not alkaline.

Comparative Example 2

The measurement was conducted in the same manner as in Comparative Example 1 except that an electrophoresis solution 7 below was used instead of the electrophoresis solution 1, and a positive electrode was brought into contact with the sample reservoir 11 and a negative electrode was brought into contact with the running buffer reservoir 12.

[Electrophoresis Solution 7]
  100 mM arginine
  1.0% (W/V) chondroitin sulfate C sodium (manufactured by Wako Pure Chemical Industries, Ltd.)
  0.02% (W/V) sodium azide
  3-hydroxypropanesulfonic acid (for pH adjustment) pH 9.8

Figure 7:
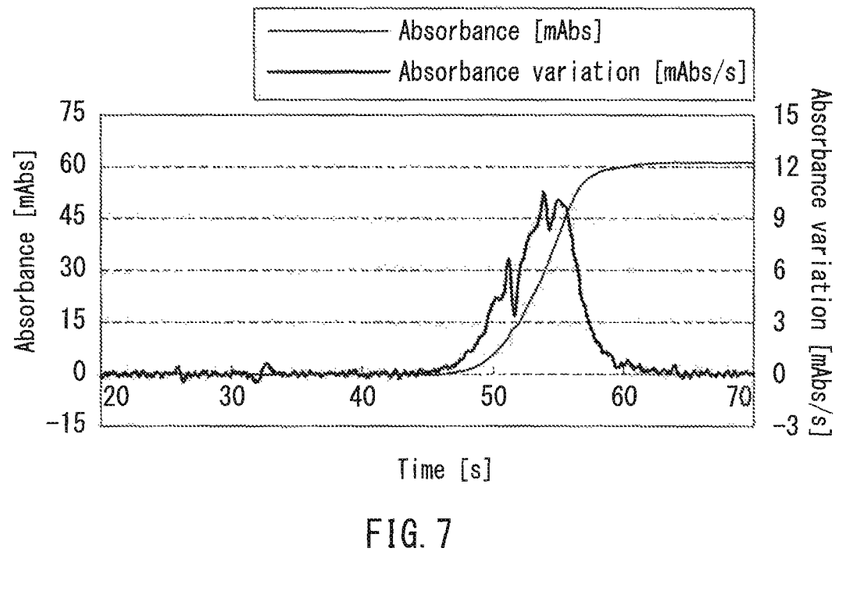
FIG. 7 is an exemplary electropherogram obtained by capillary electrophoresis in Comparative Example 2 (sample: control specimen).

FIG. 7 shows the results. As shown in FIG. 7, it was confirmed that none of HbA2, HbS, HbA, and HbF were separated by the electrophoresis solution containing an anionic polymer instead of a cationic polymer.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for analyzing a sample, comprising separating hemoglobin in the sample by capillary electrophoresis using a capillary electrophoresis chip having a capillary channel in which a cationic substance including a quaternary ammonium salt group is fixed to an inner wall of the capillary channel, wherein
   the inner wall of the capillary channel is positively charged,
   the separation of hemoglobin is conducted in an alkaline solution containing a cationic polymer including at least one group selected from the group consisting of primary, secondary, and tertiary amino groups, and an imino group,
   a weight average molecular weight of the cationic polymer is 1,000 or more and 300,000 or less.

2. A method for analyzing a sample using a capillary electrophoresis chip having a capillary channel, comprising:
   filling the capillary channel with a running buffer which is an alkaline solution containing a cationic polymer including at least one group selected from the group consisting of primary, secondary, and tertiary amino groups, and an imino group,
   wherein a cationic substance including a quaternary ammonium salt group is fixed to an inner wall of the capillary channel;
   introducing a sample into the capillary channel filled with the running buffer;
   applying a voltage to a whole or a part of the capillary channel for capillary electrophoresis so as to separate hemoglobin in the sample; and
   a weight average molecular weight of the cationic polymer is 1,000 or more and 300,000 or less.

3. The method for analyzing a sample according to claim 1, further comprising preparing the sample using the alkaline solution containing a cationic polymer.

4. The method for analyzing a sample according to claim 2, further comprising preparing the sample using the alkaline solution containing a cationic polymer.

5. The method for analyzing a sample according to claim 1, wherein the cationic polymer includes at least one selected from the group consisting of primary, secondary and tertiary amino groups.

6. The method for analyzing a sample according to claim 2, wherein the cationic polymer includes at least one selected from the group consisting of primary, secondary and tertiary amino groups.

7. The method for analyzing a sample according to claim 1, wherein a pH of the alkaline solution is in a range from 7.5 to 12.0.

8. The method for analyzing a sample according to claim 2, wherein a pH of the alkaline solution is in a range from 7.5 to 12.0.

9. The method for analyzing a sample according to claim 1, wherein the alkaline solution further includes one selected from the group consisting of a non-detergent amphoteric ionic substance, a pH buffer substance, and a combination thereof.

10. The method for analyzing a sample according to claim 2, wherein the alkaline solution further includes one selected from the group consisting of a non-detergent amphoteric ionic substance, a pH buffer substance, and a combination thereof.

11. The method for analyzing a sample according to claim 2, further comprising causing a liquid flow from a negative electrode side toward a positive electrode side in the capillary channel.

12. The method for analyzing a sample according to claim 2, further comprising bringing a negative electrode into contact with a sample introduction side and applying a voltage thereto.

13. A sample analysis kit, comprising:
a container containing a capillary electrophoresis solution that is an alkaline solution containing a cationic polymer including at least one group selected from the group consisting of primary, secondary, and tertiary amino groups, and an imino group; and
an electrophoresis chip having a sample reservoir, a running buffer reservoir, and a capillary channel connecting the sample reservoir and the running buffer reservoir,
wherein a cationic substance including a quaternary ammonium salt group is fixed to an inner wall of the capillary channel, and
a weight average molecular weight of the cationic polymer is 1,000 or more and 300,000 or less.

14. The sample analysis kit according to claim 13, wherein a pH of the alkaline solution is in a range from 7.5 to 12.0.

15. The sample analysis kit according to claim 13, wherein the alkaline solution further includes one selected from the group consisting of a non-detergent amphoteric ionic substance, a pH buffer substance, and a combination thereof.

* * * * *